(12) United States Patent
Bouchard

(10) Patent No.: US 11,099,187 B2
(45) Date of Patent: Aug. 24, 2021

(54) PROCESS FOR DETERMINING A HUMORAL RESPONSE IN AN IMMUNODEPRESSED PATIENT

(71) Applicant: BIOMERIEUX, Marcy-l'Etoile (FR)

(72) Inventor: Ghislaine Bouchard, Lyons (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 320 days.

(21) Appl. No.: 16/069,918

(22) PCT Filed: Jan. 12, 2017

(86) PCT No.: PCT/FR2017/050068
§ 371 (c)(1),
(2) Date: Jul. 13, 2018

(87) PCT Pub. No.: WO2017/121963
PCT Pub. Date: Jul. 20, 2017

(65) Prior Publication Data
US 2019/0011446 A1    Jan. 10, 2019

(30) Foreign Application Priority Data
Jan. 14, 2016 (FR) ...................................... 1650280

(51) Int. Cl.
*G01N 33/53* (2006.01)
*G01N 33/569* (2006.01)
*G01N 33/543* (2006.01)

(52) U.S. Cl.
CPC . *G01N 33/56983* (2013.01); *G01N 33/54306* (2013.01); *G01N 33/54393* (2013.01); *G01N 33/569* (2013.01); *G01N 2469/20* (2013.01); *G01N 2800/26* (2013.01); *Y02A 50/30* (2018.01)

(58) Field of Classification Search
None
See application file for complete search history.

(56) References Cited

U.S. PATENT DOCUMENTS 4,279,885 A * 7/1981 Reese ............... G01N 33/54306
424/1.85
2009/0280140 A1* 11/2009 Laal ................... G01N 33/5695
424/190.1

FOREIGN PATENT DOCUMENTS

CN    104330572 A    2/2015

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, 2014, pp. 1-7. (Year: 2014).*
RayBiotech, Inc., RayBio Rat Cytokine Antibody Array, Jun. 14, 2009, pp. 1-17. (Year: 2009).*
Lucia et al., Human cryptosporidiosis: detection of specific antibodies in the serum by and indirect immunofluorescnce, Rev. Saude Publica, 30 (5): 1996, pp. 395-402. (Year: 1996).*
International Search Report, dated May 11, 2017, corresponding to Application No. PCT/FR2017/050068.
Macedo De Oliveira, et al., "Sensitivity of second-generation enzyme immunoassay for detection of hepatitis C virus infection among oncology patients", Journal of Clinical Virology, vol. 35, No. 1, Jan. 2006, pp. 21-25, XP028038053.
Zhang, Sean X., "Non-Culture-Based Methods in Diagnostic Mycology", Clinical Microbiology Newsletter, vol. 34, No. 13, Jul. 1, 2012, pp. 101-105, XP028495139.
Haut Conseil de la Santé publique, Vaccinations des personnes immunodéprimées ou aspléniques Recommandations, Rapport 2012.

* cited by examiner

*Primary Examiner* — Gary Counts
(74) *Attorney, Agent, or Firm* — Ladas & Parry LLP; Malcolm J. MacDonald

(57) ABSTRACT

A determination method for determining, in an immunodepressed subject, a humoral response due to the presence of a target infectious agent, by detection, in a biological sample of the subject, of at least one target antibody that is susceptible of being produced by the subject when the latter is infected with or has been infected with the target infectious agent. Also, a determination method for determining a humoral response due to the presence of a target infectious agent from a biological sample from an immunodepressed or non-immunodepressed subject, in which the dilution ratio of the sample is selected as a function of the immunodepressed condition or otherwise of the subject concerned.

12 Claims, No Drawings
Specification includes a Sequence Listing.

PROCESS FOR DETERMINING A HUMORAL RESPONSE IN AN IMMUNODEPRESSED PATIENT

REFERENCE TO SEQUENCE LISTING SUBMITTED VIA EFS-WEB

This application includes an electronically submitted sequence listing in .txt format. The .txt file contains a sequence listing entitled "409435-2 ST25.txt" created on Feb. 25, 2021, and is 4,795 bytes in size. The sequence listing contained in this .txt file is part of the specification, and is hereby incorporated by reference herein in its entirety.

The present invention relates to the field of methods of detecting a humoral response in a subject in response to an infectious agent. The invention is intended for immunodepressed subjects.

BACKGROUND OF THE INVENTION

In response to a foreign substance, in particular to an infectious agent (bacteria, viruses, fungi, and parasites), a subject's organism triggers an immune response. The humoral response corresponds to the production of immunoglobulins (antibodies). These immunoglobulins diffuse into the subject's blood, tissues, or mucous membranes and allow the organism to defend itself against the infectious agent. Such a defense may be in the form of a capacity to neutralize or to prevent reproduction of the infectious agent or a new infection by the infectious agent.

Currently, a non-negligible fraction of the population is in an immunodepressed situation. This immunodepression is the consequence of a variety of clinical situations, which in particular include congenital immunodeficiencies, deficiencies due to ageing of the immune system (immunosenescence), which is observed from over 65 years of age, deficiencies linked to various diseases (diabetes, chronic inflammatory reaction, neoplasia, hemopathy, chronic hepatopathy, HIV infection, chronic renal insufficiency, etc), immunodeficiencies induced by certain medical treatments (corticotherapy, interferon, immunosuppressor treatment accompanying graft acceptance, etc), or surgical interventions (splenectomy).

The immunodepressed patient has a greater susceptibility to viral, bacterial, and/or fungal infectious agents, and for this reason needs medical care that is suitable both as regards strategies and diagnostic tools, as well as for prophylactic or therapeutic treatments. Every immunodepression situation is complex and is characterized by a specific immunological profile.

In vitro diagnostic tests (IVD) are one of the tools used to detect immunoglobulins (antibodies) specific for an infectious agent and to determine the humoral response of a subject to said infectious agent. An IVD test produces a detection result that is negative (absence of humoral response, corresponding to a result considered to be an absence of antibodies), or positive (presence of humoral response corresponding to a result considered to be the presence of antibodies), with negative results (specificity of the test) and positive results (sensitivity of the test) being separated by a positivity threshold or reference signal.

Ahead of a programmed immunosuppression (graft, splenectomy, for example), it is possible to ensure that the patient is protected by means of certain vaccinations against infections. The quality of the vaccine protection is ensured by the presence of specific immunoglobulins that can be evaluated by the result of the corresponding IVD test.

However, it is known that immunosuppression may be responsible for the regression, or even the disappearance, of vaccine immune protection (Haut Conseil de la Santé Publique, Vaccination des personnes immunodéprimées or aspléniques; Recommandations; Rapport 2012 [Public Health Council, Vaccination of immunodepressed or asplenic individuals; Recommendations; Report, 2012]).

Regression care can be carried out using successive IVD test results. For this specific aftercare, the IVD test could be rendered erroneous when the patient's situation changes, bringing up results with values that are usually recognized for the normal population.

In fact, an IVD test declares sensitivity and specificity measurements validated for cohorts of samples that are judged to be representative of the normal population.

Serums, or more generally samples from immunodepressed patients, respond differently in diagnostic tests targeting an infectious agent. In fact, immunosuppression may be responsible for a reduction to a greater or lesser extent in the quantity of immunoglobulin, and this immunoglobulin deficit could be at the origin of an erroneous response to the test. The immunodepressed population is not representative of the normal population and the positivity threshold for the test, determined with normal population samples, is no longer pertinent. (see in particular Zhang et al., *Clin. Microbiol. Newslett.* 2012, 34, 13, 101-105 and Macedo de Oliveira et al., *J. Clin. Virol.* 2006, 35, 21-25).

The development of specific tests for the immunodepressed population is difficult, because immunosuppression is statistically not normal, corresponds to an individual situation, has intensity that varies both quantitatively and qualitatively and, moreover, is transitory in nature if it is induced by a one-off immunosuppressor treatment or a non-chronic pathology. However, immunodepressed patients, who are more sensitive to infection, have a need for specific diagnostic tests in which the positivity threshold is also representative, despite the specificity of the situation.

The technical problem that is to be solved by the invention is that of enabling the person skilled in the art to take a kit or a device for detecting the humoral response as initially intended for a non-immunodepressed population, and use it on an immunodepressed population, without changing the detection reagents of the kit or device.

In this context, the invention provides a determination method for determining, in an immunodepressed subject, a humoral response due to the presence of a target infectious agent, by detection in a biological sample E1 of said subject, of at least one target antibody that is susceptible of being produced by said subject, or, more precisely, by the organism of said subject, when the latter is infected with or has been infected with said target infectious agent, the method comprising the following steps:

a) providing a volume V1 of the sample E1;

b) diluting the volume V1 with a volume D1 of diluent, with a dilution ratio R1 that is equal to V1/(V1+D1), the dilution ratio R1 being higher than a dilution ratio R2 used for a non-immunodepressed subject, R2 being equal to V2/(V2+D2), with V2 and D2 respectively being the volume of the sample E2 and the volume of diluent used for a non-immunosuppressed subject, in a manner such as to obtain a diluted sample; and c) detecting said at least one target antibody on the resulting diluted sample in order to draw a conclusion concerning the possible presence of the humoral response.

The invention proposes using the same kit or the same device for in vitro detection of antibodies, validated for use on a normal population, also to render a result that is reliable in patients in an immunodepressive situation as well.

The detailed description below enables the invention to be better understood.

The method of the invention uses a kit or device adapted to antibody detection and thus to detecting a humoral response in a subject. The term "kit" means a set of reagents necessary for detection and that are for use with an instrument that may or may not include electronic components. The term "device" means a combination both of the reagents necessary for detection and the instrument for deploying them.

In the context of the invention, the detected humoral response is due to the current or past presence of the infectious agent bringing about such a response. The term "infectious agent" means a pathogenic biological agent responsible for an infection or infestation, and thus includes viruses, bacteria, parasites, and fungi, in particular lower (or microscopic) fungi.

The bacteria may be aerobic or anaerobic. Particular mention may be made of the bacteria *Clostridium difficile, Helicobacter pylori, Mycoplasma pneumoniae, Treponema pallidum* (responsible for syphilis) and *Borrelia burgdorferi sensu lato* (responsible for Lyme disease).

Examples of viruses that may be mentioned are the virus responsible for rubella, cytomegalovirus (CMV), herpes virus (HHV-1 to HHV-8), the virus responsible for measles, the virus responsible for mumps, the virus responsible for chicken pox, hepatic viruses: HBV, HCV, HAV and HEV, the HIV virus, Epstein-Barr virus, EBV (mononucleosis), the West Nile virus, dengue virus, and papillomavirus, and in particular HPV-16 and HPV-18.

The fungi may be unicellular (yeasts) or multicellular (filamentous fungi or molds). Examples of fungi that may be mentioned are *Candida* and in particular *Candida albicans*, *Cryptococcus* and in particular *Cryptococcus neoformans*, and *Aspergillus* and in particular *A. fumigatus, A. niger, A. nidulans, A. flavus, A. clavatus*.

Parasites, i.e. organisms of various sizes that live at the expense of another organism, may be ectoparasites or endoparasites, more precisely arthropods or helminths such as pinworm, tapeworm, roundworm that cause ascariasis, Schistosoma that causes bilharziasis, liver fluke, and protozoa. More particular examples of parasites that may be mentioned are the parasites *Toxoplasma gondii* (parasite responsible for toxoplasmosis) and *Trypanosomia cruzi* (parasite responsible for Chagas disease).

In the context of the invention, the detection of antibodies is carried out in vitro. The antibodies detected may be the immunoglobulins IgM and/or IgG and/or IgE and/or IgA.

The method of the invention relates to detecting antibodies in immunodepressed subjects. The term "subject" means an animal or human subject. The term "immunodepressed subject" means a subject with an immunodeficiency compared with a patient said to be normal. In general, an immunodepressed subject belongs to one or another of the following categories:

subjects with a congenital immunodeficiency. This could be:
a deficiency said to be pure, corresponding in particular to a primitive CD4 or CD8 deficiency, an IL-2 deficiency or a deficiency in signal transduction;
a deficiency said to be combined, corresponding in particular to a mutation in the gamma chain of the IL-2 receptor, to a deficiency in the expression of CMH-II molecules, to ataxia-telangiectasia (Louis-Bar syndrome), to a deficiency in RAG enzymes or in Artemis protein necessary to VDJ recombination;
a selective IgA or IgG2 deficiency;
a hyper IgM syndrome;
hypo- or agammaglobulinemia linked to sex or Bruton's disease;
hypogammaglobulinemia of common variable expression;
a selective immunoglobulin deficiency;
a 22q11 microdeletion or Di George syndrome;
Hong and Good syndrome;
Nezelof syndrome;
a purine nucleoside phosphorylase deficiency;
an isolated deficiency of T lymphocytes;
a combined severe immunodeficiency due to adenosine deaminase deficiency;
a denuded lymphocytes syndrome;
congenital amegakaryocytosis with T and B line development anomalies; and
Wiskott-Aldrich syndrome;

subjects presenting a common variable immunodeficiency. This may in particular be:
cyclic neutropenia;
Shwachman-Diamond syndrome;
myelodysplastic syndrome;
a chemotactic deficiency, such as Chediak-Higashi disease or hyperIgE syndrome (Buckley);
a phagocytosis deficiency;
a bactericidal deficiency such as a chronic septic granulomatosis or myeloperoxidase deficiency; and
a deficiency in the gamma interferon/interleukin 12 axis;

subjects presenting with immunosenescence: concerns males and females over 65 years of age (natural decline in immune reactivity), or experiencing oxidative stress;

subjects presenting with traumatic stress;

subjects presenting with one or more metabolic disorders affecting the immune system. Some of these disorders that can be mentioned are:
protein calorie malnutrition;
oligo-element and vitamin deficiency;
chronic renal insufficiency, nephrotic syndrome;
diabetes;
chronic inflammation such as intestinal disorders, joint disorders or polyarthritis;
sarcoidosis, a non-malignant disease of the lymphoid system (cellular deficiency);
malignant hemopathies such as acute leukemia, chronic lymphoid leukemia, malignant lymphoma, multiple myeloma and Waldenström disease;
thymic anomalies such as thymoma (benign tumor of the thymus) and thymic hypoplasia;
macrophage and polynuclear activity deficiencies, such as septic granulomatosis, myeloperoxidase deficiency, Chediak Higashi syndrome, actin dysfunction and Shwachman syndrome;
complement protein deficiency;
neoplasias (cancers); and
seropositivity HIV (AIDS);

subjects who have undergone or who are being treated allopathically, inducing an immunodeficiency, such as corticotherapy, a TNF alpha inhibitor treatment (known as anti-TNF alpha), a treatment inhibiting one of the interferons, chemotherapy, radiotherapy, immunosuppressor treatment preparatory to an allograft, a post-graft immunomodulator treatment or an immunosuppressor treatment for autoimmune diseases; and subjects who have undergone surgical splenectomy.

Congenital immunodeficiencies are rare, heterogeneous, premature, and severe. They have a prevalence of 1/50000. The only treatments are allograft and gene therapy. Subjects of this type are, for example, children diagnosed with a congenital immunodeficiency, or "bubble kids", who need a compatible bone marrow graft that could restore immunological competence.

Variable common immunodeficiencies are the most frequent of the PIDs (primitive immunodeficiencies corresponding to a set of more than 200 diseases due to dysfunction of certain components of the immune system in the adult. Their prevalence varies as a function of ethnicity and is 1/20000 in France).

In 2014, 8.3% of the world population was aged 65 or over. This percentage, which will increase in future years, will increase the number of cases of immunosenescence.

Determining the humoral response and thus detecting antibodies is of great importance for immunodepressed patients. Antibody detection is conventionally carried out using a biological sample obtained form a subject of interest, after dilution of said sample. The contribution of the method of the invention is to provide the user with a kit or a device for detecting antibodies directed against an infectious agent, with at least two dilution ratios in order to obtain a "diluted" sample that is submitted for detection: one corresponding to a population that is said to be non-immunodepressed, and the other corresponding to a population that is said to be immunodepressed. Depending on the information known regarding the subject from whom the biological sample was obtained, the dilution ratio that is adapted to the immunodepressed condition or otherwise of the subject should be selected and used. When the sample derives from an immunodepressed subject, the dilution ratio corresponding to a population that is said to be immunodepressed should be used.

BRIEF SUMMARY OF THE INVENTION

The method for determining a humoral response due to the presence of a target infectious agent of the invention in an immunodepressed subject thus comprises the following characteristics:

providing a kit or device for detecting antibodies directed against said infectious agent, which is thus capable of determining the humoral response due to the presence of said target infectious agent in a subject;

providing a diluent in order to dilute the test samples, said diluent possibly forming part of the kit or detection device;

providing a dilution ratio R2 that is equal to $V2/(V2+D2)$, adapted to a population of non-immunodepressed subjects;

providing a dilution ratio R1 that is equal to $V1/(V1+D1)$, adapted to a population of immunodepressed subjects, with $R1>R2$;

selecting the dilution ratio R1, taking into account the immunodepressed condition of the subject from whom the sample to be analyzed has been obtained.

The invention also provides a determination method for determining a humoral response due to the presence of a target infectious agent starting from a biological sample from an immunodepressed or non-immunodepressed subject, in which the dilution ratio of the sample is selected as a function of the immunodepressed or non-immunodepressed condition of the subject concerned. More precisely, the invention also provides a determination method for determining a humoral response due to the presence of a target infectious agent in an immunodepressed or non-immunodepressed subject, by detecting, in a biological sample of said subject, at least one target antibody that is susceptible of being produced by said subject when the latter is infected or has been infected by said target infectious agent, the method being characterized in that it has the following characteristics:

providing a kit or device for detecting antibodies directed against an infectious agent, which is thus capable of determining the humoral response due to the presence of said target infectious agent in a subject;

providing a diluent in order to dilute the test samples, said diluent possibly forming part of the kit or detection device;

providing a dilution ratio R2 that is equal to $V2/(V2+D2)$, adapted to a population of non-immunodepressed subjects;

providing a dilution ratio R1 that is equal to $V1/(V1+D1)$, adapted to a population of immunodepressed subjects, with $R1>R2$;

selecting the dilution ratio used as a function of the immunodepressed condition or otherwise of the subject from whom the sample to be analyzed has been obtained: R1 is used if the subject is immunodepressed and R2 is used if the subject is not immunodepressed.

DETAILED DESCRIPTION OF THE INVENTION

In this context, the invention proposes adapting the dilution ratio used for a sample obtained from an immunodepressed subject, in a manner such that it differs from the ratio used for a sample obtained from a non-immunodepressed subject. In accordance with the invention, a volume V1 of a sample E1 to be tested obtained from an immunodepressed subject is diluted with a volume D1 of diluent, with a dilution ratio R1 that is equal to $V1/(V1+D1)$, the dilution ratio R1 being higher than a dilution ratio R2 used for a non-immunodepressed subject. R2 is equal to $V2/(V2+D2)$, in which V2 and D2 are respectively the volume of the sample E2 and the volume of diluent used for a non-immunodepressed subject. In contrast, the diluent used is the same regardless of whether the sample to be tested is a sample E1 obtained from an immunodepressed subject or a sample E2 obtained from a non-immunodepressed subject. A diluted sample is then obtained and at least one target antibody is detected therein in such a manner such as to be able to conclude whether or not the desired humoral response is present in said subject. The detection may be carried out on the entire diluted sample obtained or on only a portion thereof.

The subject from whom the sample is obtained is a human or animal subject. Clearly, the immunodepressed subject from whom the sample E1 is obtained and the non-immunodepressed segment from whom the sample E2 is obtained should belong to the same species: in particular, for a kit or device intended for a human subject, a human sample should be used, and for a kit or a device intended for an animal, a sample from an animal from the same species should be used.

Advantageously, in the context of the invention, the dilution ratio R1 for a sample E1 to be tested obtained from an immunodepressed subject is defined as follows:

$$1.5R2 \leq R1 \leq 5R2,$$

R2 being the dilution ratio used for a sample E2 obtained from a non-immunodepressed subject. The dilution ratios R1 and R2 should usually be selected from a range of 0.01 to 0.9.

Conventionally, the diluent used to dilute the biological sample to be tested is a liquid solution that does not alter the immunological reactivity of the antibodies being investigated. Examples of suitable diluents that may be mentioned are animal serums such as bovine, equine, or sheep serum, buffers, in particular Tris, phosphate, or HEPES, or indeed water. Whatever the diluent that is used, it could include one or more additives, for example selected from: polymers such as PEG, detergents such as TWEEN® surfactant, proteins, sugars and lipids, and/or one or more reagents that can ensure detection, in particular of a binding partner for the antibody to be detected and, for example, a labeled binding partner, as is explained below.

In accordance with a first implementation, the increase in the dilution ratio R1 used for a sample E1 to be tested obtained from an immunodepressed subject compared to the dilution ratio R2 used for a sample E2 obtained from a non-immunodepressed subject is obtained by increasing the volume V1 of the sample E1 compared to the volume V2 of the sample E2 used for a non-immunodepressed subject.

In accordance with a second implementation, the increase in the dilution ratio R1 used for a sample E1 to be tested obtained from an immunodepressed subject compared to the dilution ratio R2 used for a sample E2 obtained from a non-immunodepressed subject is obtained by reducing the volume D1 of diluent compared to the volume D2 of diluent used for a non-immunodepressed subject.

The person skilled in the art is able to determine the ratios of sample volume to diluent volume as a function of the device used and of the detection method employed. As an example, when using a VIDAS® device, sample volume to diluent volume ratios in the range from 1/100 to 50/100 could be used.

The method of the invention may be carried out on any type of biological sample obtained from a subject (blood, urine, feces, saliva, etc), but is in particular adapted to samples of blood, total blood, serum, or plasma.

The sample may be pre-treated prior to diluting it, for example in order to inactivate the infectious agent, to dissociate the immune complexes, to neutralize the analytes that are not specific to the reaction, or to make the antibodies available to the binding partners used in the method for determining the humoral response. Examples of pre-treatments of this type are heating, acidification, reduction, oxidation, the use of one or more chaotropic agents, of one or more chelating agents, mechanical processes such as filtration, centrifuging, or sonication, and combinations thereof.

The detection carried out in step c) comprises both affinity reactions of the antibodies to be detected with one or more detection reagents, and also demonstrating said reaction. The detection reagent used is a binding partner for the antibody to be detected, optionally in combination with another reagent. The affinity reaction or reactions could be carried out in a manner that is concomitant with the dilution step when the diluent includes a binding partner for the antibody to be detected. The detection includes a step for incubation between the diluted sample and one or more detection reagents and may also include one or more washing steps and/or revealing steps in order to manifest the presence of antibody.

The target antibody or antibodies may be detected in step c) in a quantitative manner: this is then termed an assay or quantification; or it may be qualitative. As an example, the detection could be carried out using a biochemical test, in particular an immunological test (termed an immunoassay) using at least one binding partner for the antibody to be detected.

The term "qualitative" means a positive or negative response concerning the presence of the antibody of interest, which may optionally be numerical, with no relationship to the exact concentration of the antibody of interest, since there is no comparison with a calibration curve, as there is with quantitative detection (see below).

The term "quantitative" means that the concentration of at least one antibody of interest is determined. Conventionally, in order to determine the quantity of at least one antibody in a biological sample, the signal that is proportional (for a direct detection method) or inversely proportional (for an indirect method) to the quantity of said antibody could be compared with a calibration curve that has already been obtained using techniques that are widely known to the person skilled in the art. Thus, for example, the calibration curve may be obtained by carrying out an assay using the same antibody, as well as increasing quantities of that antibody. A curve is then obtained by plotting the concentration of the antibody of interest along the abscissa, and the corresponding signal obtained after assay up the ordinate.

In the context of the invention, it is possible to use any kit or device that is adapted to antibody detection and thus to detecting a humoral response in a subject. In particular, at least said target antibody is detected in step c) using direct or indirect immunoassay, in particular an ELISA or ELFA test.

Clearly, the prefix "immuno" in the term "immunoassay", for example, in the present application should not be considered as strictly indicating that the binding partner is necessarily a partner with an immunological origin. Thus, it is known to refer to an ELISA test for tests that use binding partners that are not immunological in the strictest sense, and more widely known as a "ligand binding assay"; the term "immuno" is included in the term for which ELISA is an acronym. For the purposes of clarity and uniformity, the term "immuno" is employed in the present application to designate any biological analysis using at least one binding partner adapted to bind to an antibody of interest.

The binding partner used should preferably be specific, i.e. it should be capable of binding to the antibody of interest, with a high specificity, preferably with a specificity of more than 90%, or even a specificity of 100%, in particular when it is capable of binding exclusively or almost exclusively to the antibody of interest. A binding partner is said to be non-specific when its binding specificity to the antibody of interest is low and it is then capable of binding to other ligands such as other antibodies.

Antigens are examples of binding partners for antibodies. It is also possible to use anti-immunoglobulin antibodies as a binding partner, as well as their fragments or their analogs. Examples of fragments of antibodies that may be mentioned are Fab, Fab', F(ab')2 fragments as well as scFv ("Single chain variable fragment"), dsFv ("Double-stranded variable fragment"). These functional fragments may in particular be obtained by genetic engineering.

The antibody analogs may be nanofitins, aptamers, or DARPins.

Nanofitin antibody analogs are small proteins that, like antibodies, are capable of binding to a biological target (and in particular to an antibody), thus enabling it to be detected, captured, or quite simply to target it in an organism.

Aptamer antibody analogs are oligonucleotides, generally RNA or DNA, identified in libraries containing up to $10^{15}$ different sequences, using an in vitro combinatorial selection method known as SELEX, "Systematic Evolution of Ligands by Exponential Enrichment" (Ellington A D. and Szostak J W., 1990 Nature, 346: 818-822). The majority of aptamers are composed of RNA because of the capacity of the RNA to adopt various and complex structures, which means that cavities with a variety of geometries can be created at its surface, allowing various ligands to bind. They are biochemical tools of interest that may be used in biotechnological, diagnostic or therapeutic applications. Their selectivity and their binding properties are comparable with those of antibodies.

"DARPins", standing for Designed Ankyrin Repeat ProteINS (Boersma Y L and Plütckthun A, 2011 Curr. Opin. Biotechnol, 22: 849-857) antibody analogs, are another class of proteins that can be used to mimic the antibodies and can bind with a high affinity and selectivity to target proteins (and in particular to an antibody). They derive from the family of ankyrin proteins, which are adaptive proteins that can fix the membrane proteins integral to the spectrin/actin network that constitutes the "backbone" of the plasmatic cell membrane. The structure of ankyrins is based on the repetition of a motif of approximately 33 amino acids and it is the same for DARPins. Each motif has a secondary structure of the "helix-turn-helix" type. DARPins contain at least three, preferably four to five repeated motifs, and they are obtained by screening combinatorial libraries.

In the method of the invention, the optionally specific antibody or antibodies under investigation may be used as capture reagents, as detection reagents, or as capture and detection reagents.

Immunological reactions, i.e. the antibody and binding partner bond, may be visualized using any detection means, in particular by labeling or surface plasmon resonance.

The term "labeling" means attaching a label reagent that is capable of directly or indirectly generating a detectable signal. A non-limiting list of these label reagents consists of:

enzymes that produce a detectable signal, for example by colorimetry, fluorescence, luminescence, such as horseradish peroxidase, alkaline phosphatase, β-galactosidase, glucose-6-phosphate dehydrogenase;

chromophores such as fluorescent, luminescent, dye compounds;

radioactive molecules such as $^{32}P$, $^{35}S$ or $^{125}I$;

fluorescent molecules such as Alexa or phycocyanins; and electrochemiluminescents, such as organometallic derivatives based on acridinium or ruthenium.

At least one antibody of interest may be detected in a direct manner, i.e. by labeling the binding partner, or in an indirect manner, i.e. using an anti-ligand of the binding partner (ligand).

Ligand/anti-ligand pairs are well known to the person skilled in the art; by way of example, this applies to the following pairs: biotin and streptavidin, haptene and antibody, antigen and antibody, peptide and antibody, sugar and lectin, polynucleotide and polynucleotide complement. The ligand then carries the binding partner for the target antibody. The anti-ligand may be detectable directly using the reactive labels described in the above paragraph, or it may itself be detectable using a ligand and anti-ligand pair.

Under certain conditions, such indirect detection systems may lead to amplification of the signal. This technique for signal amplification is well known to the person skilled in the art and reference in this regard may be made to the Applicant's earlier patent applications FR 2 781 802 or WO 95/08000.

Depending on the type of labeling used, the person skilled in the art adds reagents allowing the labeling to be visualized or allowing a signal to be emitted that can be detected by any appropriate type of measuring apparatus such as, for example, a spectrophotometer, a spectrofluorimeter, a densitometer, a luminometer, or indeed a high definition camera.

The binding partner that allows the antibody that is to be detected to be detected may in particular be fixed onto a solid support. In known manner, the solid support may be in any appropriate form such as a plate, a cone, a bead, the bead optionally being radioactive, fluorescent, magnetic, and/or conductive, a dilution segment, a glass tube, a well, a foil, in particular in paper format, a chip, a microtitration plate, or the like. When the support is in the form of beads, these usually have a diameter that lies in the range one hundredth of a micrometer to one nanometer. Preferably, the binding partner fixed on the support, used as a capture partner, is specific to the antibody of interest and the binding partner used for detection may or may not be specific for the antibody of interest.

Examples of immunological tests like those defined above that may be mentioned are "sandwich" methods such ELISA, ELFA, IRMA, and RIA, methods known as competing methods, and direct immunodetection methods such as immunohistochemistry, immunocytochemistry, Western blot, and dot blot.

Antibody detection methods using two binding partners are sandwich methods that are well known to the person skilled in the art, namely:

a method generally known as double antigen sandwich, using the capture and detection of two antigens, of identical or different natures, which are capable of being recognized by the antibody being investigated;

a method generally known as immunocapture, using an antibody, an antibody fragment or an antibody analog as described above for capture, and an antigen for detection; and a method generally known as indirect sandwich, using an antigen for capture and an antibody, an antibody fragment, or an antibody analog for detection.

Immunochromatography is also known as lateral flow immunoassay. The devices generally used in such tests comprise a diffusion medium, which is generally immobilized on a support, and that allows the liquid sample, to migrate. Conventionally, several zones can be distinguished in the diffusion medium, namely a zone for application of the liquid sample, a labeling zone, and a reaction zone, the reaction zone usually including a visualization zone (also known as the capture zone) and a control zone. These various zones are in fluid communication. Thus, the target antibody, if it is present in the sample disposed at the application zone, binds to a first labeled binding partner at the labeling zone, then the complex formed thereby migrates to the reaction zone where it is immobilized in the capture zone by reaction with a second binding partner bound to the diffusion medium, and the user can determine whether the antibody is in fact present by the manifestation of a detectable signal that is determined by the type of labeling associated with the first binding partner. In general, the presence of the target antibody in the sample is manifested in the form of a detectable line, usually known as the test line. In general, the reaction zone also comprises a zone for monitoring migration of the sample, in order to indicate to the user that the sample has migrated correctly through the diffusion medium upstream of the visualization zone. This may, for example, be carried out by revealing a control line with a predetermined color. Patent applications WO 2004/003559, WO 2006/092103, WO 2007/081330, US 2004/0161859, and WO 2012/172232, which describe such devices, may be mentioned by way of example.

In particular, the detection of step c) may be carried out by means of a short-duration test, in particular by ELISA, ELFA, and immunochromatographic tests. In particular, the period between the start of dilution in step b) and reaching the conclusion in step c) is 2 hours (h) or less, preferably 1 h and 30 minutes (min) or less, and more preferably 1 h or less. Preferably, this period is 45 min, 30 min, 20 min, 15 min, 10 min, or 5 min. For an ELISA/ELFA test, it is preferable to use a period of 20 min to 45 min, and for an immunochromatographic test, it is preferable to use a period of 5 min to 15 min.

Advantageously, the method of the invention is carried out by means of an automated test with a defined incubation period, in contrast to a non-automated test of the microplate type, or it may be carried out by immunochromatography.

Examples of devices (also known as instruments) that may be used to carry out the method of the invention and that may be mentioned are the following in vitro devices and diagnostic instruments: Architect® marketed by Abbott diagnostics, Cobas® and Elecsys® marketed by Roche Diagnostics, Liaison® marketed by Diasorin and VIDAS® marketed by bioMérieux; they all have a range of infectious diagnostic tests. These various instruments comprise a program dedicated to toxoplasmosis/rubella/CMV/herpes for monitoring pregnant women, a pediatric program for diagnosing infections and/or for monitoring vaccination for the measles/mumps/chicken pox viruses, a hepatitis program for diagnosing infections and/or for monitoring vaccination for the HBV, HCV, HAV, HEV viruses, an HIV program for diagnosing infections by the HIV virus. They are also adapted to detecting infections by the EBV virus (mononucleosis), detecting infections by *Borrelia burgdorferi sensu lato* (Lyme disease), detecting infections by *Clostridium difficile*, detecting infections by *Helicobacter pylori*, detecting infections by *Mycoplasma pneumoniae*, detecting infections by the West Nile virus, detecting infections by *Trypanosomia cruzi* (Chagas), detecting infections by *Treponema pallidum* (syphilis), or indeed detecting infections by the dengue virus.

The detection carried out in step c) results in a signal that can be detected. The conclusion reached in step c) is conventionally made by comparing that signal with a reference signal. In particular, the conclusion as to the possible presence of the humoral response is be positive if the signal obtained is higher than a reference signal S1.

The term "reference signal" means a value or range of values used in order to determine whether the conclusion of the determination method of the invention is positive (it is considered that a humoral response is present in the subject from whom the sample has been obtained) or negative (it is considered that a humoral response is absent from the subject from whom the sample was obtained). The reference signal could be either a discrete value, or a range of values corresponding to a zone of uncertainty, also known as the gray zone. When the signal obtained from a sample is higher than this reference signal (upper limit of a range), it is concluded that a humoral response is present in the subject, and when the signal obtained is lower than the reference signal (lower limit of a range), it is concluded that there is an absence of humoral response in the subject. Clearly, when the measured value is within the range of uncertainty, or is very close to the reference value for a discrete value, a definitive conclusion cannot be drawn and additional investigations should be carried out. Preferably, the reference signal has a discrete value corresponding to the positivity threshold of the method.

In theory, a subject who has never been in contact with a given infectious agent will not have antibodies directed against that infectious agent. In reality, there are always non-specific cross reactivities due to the polyvalency of certain antibodies. For this reason, it is necessary to determine a reference signal corresponding to a positivity threshold that is specific to the infectious agent, which means that a positive status (presence of humoral response against said infectious agent) or negative status (absence of humoral response against said infectious agent) can be provided. This reference signal is determined over a representative population and is selected in particular in order to correspond to the value that provides the best compromise between diagnostic sensitivity and specificity. The sensitivity measures the capacity of a test to provide a positive result (TP=true positive) when antibodies are effectively produced to combat the infectious agent under consideration in a subject. A measurement of the sensitivity is always accompanied by a measurement of the specificity. This latter corresponds to the capacity to obtain a negative result (TN=true negatives) for actual absence (present or past) of the infectious agent under consideration in a subject.

By tracing the detection curves for antibody obtained as a function of the percentage of the "true negative" population specificity, and also of the true positive population (TP), a positivity threshold (reference signal) is determined that corresponds to the junction of the two curves. There often exists a zone where the TP and TN results are superimposed, such that in this range, the results are rendered ambiguous.

The position of the positivity threshold may be defined by determining the best sensitivity and specificity pair, i.e. that for which the number of FP and FN (false positive and false negative results) is the lowest. The positivity threshold of a test influences its sensitivity and its specificity. Thus, with a lowered threshold, a test is more sensitive but less specific.

The samples used to determine the reference signal are biological samples of the same nature as the biological sample to be tested, or at least of a compatible nature, in order to constitute a reference for detecting target antibodies.

Together, the sensitivity and specificity measurements of a diagnostic test characterize its intrinsic pertinence. This performance is verified during the development of a test, then validated during clinical tests on collections of samples recruited by experts in the population that is said to be normal, i.e., preferably, in the present case, in a non-imunodepressed population. The measurements are mentioned in the notes for a commercial test and obtaining results in agreement with the test measurements is linked to the conditions under which it is carried out: the sample volume, the dilution ratio of the sample analyzed during the time attributed to the reaction incubation, etc.

The position of the reference signal (positivity threshold) may depend on the use attributed to the test: a very sensitive test is especially useful for early screening of an infection or infestation (few FNs), while a highly specific test is useful for ensuring that an infection or infestation is absent, in particular for vaccine monitoring (few FPs). Thus, the person skilled in the art is able to adapt the selected reference signal as a function of the application envisaged by the method of the invention.

However, the equilibrium defined in the test is adapted only to subjects having a "normal" immune system (not immunodepressed); it is less pertinent for immunodepressed subjects. The method of the invention proposes overcoming this problem by adjusting the dilution ratio for an immunodepressed subject.

In addition, depending on the particular implementation of the method of the invention for determining a humoral response due to the presence of a target infectious agent in an immunodepressed subject, it is also proposed that the signal obtained in step c) should be compared with a specific reference signal for a population of immunodepressed subjects. In particular, the conclusion concerning the possible presence of the humoral response is positive if the signal obtained is higher than a reference signal S1, said reference signal S1 being higher than or equal to a reference signal S2 used for a sample obtained from a non-immunodepressed subject.

In other words, the method of the invention also comprises the following characteristics:

providing a reference signal S2 adapted to a population of non-immunodepressed subjects;

providing a reference signal S1 adapted to a population of immunodepressed subjects, with S1≥S2;

selecting the reference signal S1 used in order to come to a conclusion in step c) because of the immunodepressed condition of the subject from whom the test sample is obtained.

In a method of the invention for determining a humoral response due to the presence of a target infectious agent in an immunodepressed or non-immunodepressed subject, in a particular implementation, the method comprises the following characteristics:

providing a reference signal S2 adapted to a population of non-immunodepressed subjects;

providing a reference signal S1 adapted to a population of immunodepressed subjects, with S1≥S2;

selecting the reference signal used to come to a conclusion in step c) as a function of the immunodepressed condition or otherwise of the subject from whom the test sample is obtained: S1 is used if the subject is immunodepressed and S2 is used if the subject it not immunodepressed.

The reference signal S2 is then determined from the results obtained over a population of non-immunodepressed subjects, while the reference signal S1 is determined from results obtained over a population of immunodepressed subjects.

In the context of the invention, then, it is possible to use the same kit or the same device, in particular adapted to an automated process, in order to diagnose of the humoral response over a normal population and over an immunodepressed population. In this context of dual use, the dilution ratio, or even the reference signal (positivity threshold) is(are) adapted as a function of the origin of the test sample: immunodepressed subject or non-immunodepressed (normal) subject.

In accordance with the invention, said at least one target antibody is detected using a kit or a diagnostic device that is adapted to or initially intended for detecting said at least one target antibody in a biological sample from a population of non-immunodepressed subjects. It is not necessary to carry out any adaptation of the kit or device for detecting said at least one target antibody in a sample from an immunodepressed subject apart from the adaptation(s) provided in the context of the invention, namely increasing the dilution ratio, possibly accompanied by increasing the reference signal defining the positivity threshold and thus the presence of a humoral response. The detection carried out in step c) uses the same kit or the same device, and in particular the same reagents as those used for detection carried out from a sample originating from a subject said to be normal or not immunodepressed.

Advantageously, in the context of the invention, said at least one antibody is detected in step c) under the same conditions as for detection carried out starting from a biological sample E2 from a non-immunodepressed subject. It is nevertheless possible to vary certain conditions as a function of the sample (obtained from an immunodepressed or non-immunodepressed subject), in particular the time period between the start of the dilution in step b) and reaching the conclusion in step c), and in particular the incubation period, or the temperature used in step c), and in particular during incubation.

In the context of the invention, a signal is preferably detected and generated during the detection of step c) under the same conditions as those used for detecting said at least one target antibody in a sample originating from a non-immunodepressed subject. Advantageously, only the dilution ratio and optionally the reference signal is(are) modified, as described in the context of the invention, between determining a humoral response starting from a sample obtained from an immunodepressed subject and determining a humoral response starting from a sample obtained from a non-immunodepressed subject.

The detection conditions employed in step c) are familiar to the person skilled in the art. In particular, a volume of sample diluted from 5 microliter (µL) to 1 milliliter (mL), preferably 10 µL to 500 µL, and preferably 20 µL to 250 µL, could be used. The temperature used for incubation could, as is conventional, be in the range from 15° C. to 40° C., preferably 18° C. to 39° C. and is preferably equal to 37° C.

The method for determining a humoral response of a subject to an infectious agent, also termed a pathogenic agent, as proposed in the context of the invention has the following applications in particular: to aid in vitro diagnosis or to perform in vitro diagnosis of an infection by the pathogenic agent in a subject who might be infected, for the therapeutic care of a subject infected by the pathogenic agent, to carry out epidemiological studies of the seroprevalence of anti-pathogenic agent antibodies in a population or in a given geographical territory, to determine whether a subject needs to be vaccinated or revaccinated against the pathogenic agent (the investigated antibodies are then IgG). Strictly speaking, the term "infection" is used for a disease caused by a bacterium, a virus, or a fungus, and "infestation" is used for a disease caused by a parasite. However, in the context of the present description, for the purposes of simplification, the term "infected" is used to cover the term "infested", because parasites are classified as infectious agents. In particular, the method of the invention could be used to assist in vitro diagnosis or to perform in vitro diagnosis of an infection by a bacterium, a virus, a fungus, or a parasite listed in the context of the invention, or indeed for the therapeutic care of a subject infected by a bacterium, a virus, a fungus, or a parasite listed in the context of the invention. The method of the invention is particularly suitable for detecting a humoral response in an immunodepressed patient because of the presence (actual or future) of an infectious agent selected from the parasites *Toxoplasma gondii* (parasite responsible for toxoplasmosis), *Trypanosomia cruzi* (parasite responsible for Chagas disease), the bacteria *Clostridium difficile, Helicobacter pylori, Mycoplasma pneumoniae, Treponema pallidum* (responsible for syphilis), *Borrelia burgdorferi sensu lato* (responsible for the Lyme disease), the virus responsible for rubella, cytomegalovirus (CMV), the herpes virus, the virus responsible for measles, the virus responsible for mumps, the virus responsible for chicken pox, the hepatic viruses: HBV, HCV, HAV and HEV, the HIV virus, the EBV virus (mononucleosis), the West Nile virus, and the dengue virus.

The example below serves to illustrate the invention but is not in any way limiting in nature.

EXAMPLE

Detecting IgG Directed Against the Varicella Zoster Virus (VZV) in Non-Immunodepressed and in Immunodepressed Subjects Chicken pox is a very common infectious disease: 90% of children contract the infection before the age of 12. It is caused by a DNA virus from the Herpes viridae family, VZV (Varicella Zoster Virus), which is transmitted solely between humans. Chicken pox represents the primo-infection by the VZV virus and this infection causes immunity. The zoster is the clinical expression of the reactivation of VZV. The immunity acquired following primo-infection or following vaccination persists for a number of years, but in cases of immunodepression, it can be reduced, or it can be reduced in a manner linked with age.

In populations at risk, it is appropriate to look for anti-VZV IgGs in order to be able to evaluate their immune status. Such populations at risk are: care personnel, pregnant women, newborns, and the immunodepressed.

a) Preparation of a VGLE Recombinant Protein of the Varicella Zoster Virus

The gene ORF68 coding for the gE glycoprotein of the varicella zoster virus (UniProtKB accession number P09259), also known as VGLE, was used for the construction. The extra-membrane domain (amino acids 31-538 corresponding to SEQ ID N°1) of the native protein (623 amino acids in total) was fused with 6 histidines on the N-terminal side in order to enable purification by metal-chelate affinity chromatography. The sequence selected in this manner was obtained in the form of a synthetic gene cloned into an expression vector, then the plasmid was introduced into *E. coli* bacteria. After culture, the bacteria were recovered, lysed and the recombinant protein of interest was purified on Ni-NTA resin (Qiagen). After a wash cycle, the protein was eluted in the presence of an imidazole gradient, then dialyzed and quantified.

```
SEQ No 1:
SVLRYDDFHT DEDKLDTNSV YEPYYHSDHA ESSWVNRGES

SRKAYDHNSP YIWPRNDYDG FLENAHEHHG VYNQGRGIDS

GERLMQPTQM SAQEDLGDDT GIHVIPTLNG DDRHKIVNVD

QRQYGDVFKG DLNPKPQGQR LIEVSVEENH PFTLRAPIQR

IYGVRYTETW SFLPSLTCTG DAAPAIQHIC LKHTTCFQDV

VVDVDCAENT KEDQLAEISY RFQGKKEADQ PWIVVNTSTL

FDELELDPPE IEPGVLKVLR TEKQYLGVYI WNMRGSDGTS

TYATFLVTWK GDEKTRNPTP AVTPQPRGAE FHMWNYHSHV

FSVGDTFSLA MHLQYKIHEA PFDLLLEWLY VPIDPTCQPM

RLYSTCLYHP NAPQCLSHMN SGCTFTSPHL AQRVASTVYQ

NCEHADNYTA YCLGISHMEP SFGLILHDGG TTLKFVDTPE

SLSGLYVFVV YFNGHVEAVA YTVVSTVDHF VNAIEERGFP

PTAGQPPATT KPKEITPVNP GTSPLLRY
``` b) Carrying Out VIDAS Immunoassay in Order to Detect the Anti-VZV IgG

The single-use cone acted both as a solid phase for the reaction and as a pipetting system. The cartridge was composed of 10 wells (X0 to X9) covered with a sheet of aluminum, sealed, and labeled. The first well (X0) included a precut portion to facilitate introduction of the sample. The last well (X9) was an optical cell in which the fluorescence of the substrate was measured. The various reagents necessary for analysis were contained in the intermediate wells (X1 to X8). All of the steps of the test were carried out automatically by the instrument. They were constituted by a succession of cycles for aspiration/delivery of reaction medium.

The cones were sensitized with 300 µL of a solution of the VGLE recombinant protein described in a) and diluted to 3 micrograms per milliliter (µg/mL) in a 77 millimolar (mM) carbonate buffer, pH 9.2. After incubating for approximately 20 h at +18/25° C. with the sensitizing solution, the cones were emptied. Next, 300 µL of a Tris 200 mM buffer solution containing 5 g/l of bovine serum albumin (BSA) was added. Passivation of the phase was carried out at +18/25° C. overnight. The cones were emptied, dried, then stored at +4° C. until use, protected from moisture.

The automated VIDAS® instrument mixed 11.4 µL of the sample of serum or plasma to be tested in 400 µL of sample diluent containing a phosphate buffer, pH 7.4, containing 154 mM of NaCl and 5 grams per liter (g/L) of BSA. As soon as the VIDAS® came into contact with the sample, the first step of the immunological reaction commenced. This step enabled the anti-VGLE IgG present or otherwise in the serum or plasma sample to bind specifically to the viral VGLE protein adsorbed onto the cone. After incubating for 210 seconds at 37° C., the unbound components were eliminated by washing with a Tris 200 mM buffer, pH 7.8, NaCl 300 mM and 0.05% TWEEN 20® surfactant. During the second step, the cone was incubated with a solution of conjugate containing approximately 20 nanograms per milliliter (ng/mL) of a mouse IgG anti-human IgG (bioMérieux), coupled with alkaline phosphatase, in a 10 mM phosphate buffer, NaCl 154 mM, 5 g/L milk powder. The X5 wells contained 400 µL of this solution that was aspirated/delivered by the cone for 4 minutes, always at 37° C. The second step involved the formation of a complex between the anti-VGLE IgG retained on the solid phase and the anti-IgG conjugate coupled with the alkaline phosphatase. This step was followed by 2 successive washes in order to eliminate the unbound compounds.

During the final revealing step, the 4-methylombelliferyl phosphate substrate was aspirated then delivered to the cone; the enzyme of the conjugate catalyzed the reaction for hydrolysis of this substrate to 4-methylombelliferone, wherein the fluorescence emitted therefrom was measured at 450 nanometers (nm). The value for the fluorescence signal (RFV=relative fluorescence value) was proportional to the concentration of anti-VZV IgG present in the sample.

c) Results

Under the reference conditions of use, the volume of the biological sample used was 11.4 µL. Under these conditions, the reference signal allowing the positive samples (presence of a humoral response) to be distinguished from the negative samples (absence of a humoral response) was 70 RFV.

In order to increase the diagnostic sensitivity and to detect the anti-VZV IgG in immunodepressed subjects better, we increased the sample volume from 11.4 µL to 38.3 µL without modifying the volume of diluent, which was kept at 400 µL, and which corresponded to an increase by a factor of 3.1 in the dilution ratio (volume of sample) (volume of sample+diluting volume). For weakly positive samples collected from non-immunodepressed subjects, this increase in the sample volume meant that the signal obtained could be increased by an average of 215 RFV (+93 to +324 RFV), as can be seen in Table 1. In addition, the increase in the non-specific signal was only +21 RFV on average (+4 to +57 RFV). Because the specific signal increased much more than the non-specific signal, the modification in the reference signal could be discerned.

TABLE 1

Comparison of signals obtained by increasing the sample volume for non-immunodepressed subjects.

| Sample code | VIDAS signal (RFV) Sample volume 11.4 μL | VIDAS signal (RFV) Sample volume 38.3 μL | VIDAS signal (RFV) "background noise" Sample volume 11.4 μL | VIDAS signal (RFV) "background noise" Sample volume 38.3 μL |
|---|---|---|---|---|
| se48-H3 | 147 | 385 | 20 | 77 |
| se48-H8 | 72 | 206 | 9 | 23 |
| se48-H28 | 152 | 476 | 15 | 56 |
| se48-H32 | 97 | 280 | 4 | 8 |
| se48-F5 | 132 | 371 | 20 | 49 |
| se48-F11 | 154 | 425 | 28 | 66 |
| se48-F16 | 81 | 263 | 6 | 16 |
| se48-F18 | 177 | 497 | 9 | 17 |
| se48-F31 | 133 | 367 | 18 | 29 |
| se48-F32 | 155 | 425 | 19 | 33 |
| se48-F36 | 117 | 253 | 22 | 59 |
| se48-F40 | 100 | 281 | 13 | 18 |

Thus, 47 samples obtained from immunodepressed subjects (patients with transplants, immunodepressed patients following immunosuppressor treatment administered to prevent rejection of the graft) were assayed in order to determine a new reference signal adapted to the sample volume of 38.3 μL and an immunodepressed population: the new reference signal was fixed at 150 RFV. Next, the two sample volume/reference signal pairs were compared over a new panel of samples from immunodepressed subjects. Once again, it was a panel of slightly positive samples: the positivity of these samples was demonstrated with the Enzygnost microplate anti-VZV/IgG technique using a long incubation period. The results are summarized in Table 2.

Of these 32 slightly positive samples, 6 were not detected by the VIDAS test under the reference conditions (sample volume 11.4 μL). Thus, they were false negatives. Under the improved assay conditions (sample volume 38.3 μL), the number of false negatives was no more than 4. This result corresponds well to an improvement in the diagnostic sensitivity from 81% to 87%. However, it is important to note that this estimation of the sensitivity underestimates the actual sensitivity of the test. In fact, the panel used was not a diagnostic panel; it was enriched in samples that were difficult to detect.

In conclusion, an increase in the volume of the sample and the choice of a second reference signal allowed the diagnostic sensitivity of a serological diagnostic kit to be improved for immunodepressed populations without changing either the reagents of the kit or their concentrations.

TABLE 2

Comparison of immunoassays with standard sample volume and increased sample volume in immunodepressed patients

| Sample | VIDAS sample vol. 11.4 μL RFV | VIDAS sample vol. 11.4 μL Pos for RFV > 70 | VIDAS sample vol. 38.3 μL RFV | VIDAS sample vol. 38.3 μL Pos for RFV > 150 |
|---|---|---|---|---|
| 121850 | 185 | Pos | 489 | Pos |
| 121665 | 245 | Pos | 820 | Pos |
| 121852 | 218 | Pos | 524 | Pos |
| 121860 | 173 | Pos | 491 | Pos |
| 121981 | 78 | Pos | 201 | Pos |
| 121979 | 137 | Pos | 373 | Pos |
| 121986 | 181 | Pos | 430 | Pos |
| 121990 | 181 | Pos | 515 | Pos |
| 121991 | 61 | Neg | 127 | Neg |
| 121993 | 231 | Pos | 714 | Pos |
| 121994 | 132 | Pos | 297 | Pos |
| 122001 | 283 | Pos | 871 | Pos |
| 122011 | 80 | Pos | 205 | Pos |
| 122015 | 185 | Pos | 444 | Pos |
| 121606 | 132 | Pos | 378 | Pos |
| 127333 | 62 | Neg | 211 | Pos |
| 121642 | 65 | Neg | 105 | Neg |
| 122021 | 34 | Neg | 51 | Neg |
| 122022 | 59 | Neg | 170 | Pos |
| 122025 | 151 | Pos | 456 | Pos |
| 122033 | 127 | Pos | 294 | Pos |
| 122038 | 28 | Neg | 109 | Neg |
| 127107 | 147 | Pos | 375 | Pos |
| 127091 | 123 | Pos | 308 | Pos |
| 121666 | 255 | Pos | 854 | Pos |
| 43240 | 169 | Pos | 330 | Pos |
| 43255 | 252 | Pos | 649 | Pos |
| 43258 | 266 | Pos | 579 | Pos |
| 43266 | 278 | Pos | 638 | Pos |
| 43290 | 233 | Pos | 498 | Pos |
| 43314 | 261 | Pos | 608 | Pos |
| 43318 | 255 | Pos | 510 | Pos |

The invention claimed is:

1. A determination method for determining, in an immunodepressed human subject, a humoral response due to the presence of a target infectious agent, by detection, in a sample E1 of serum or plasma of said human subject, of at least one target antibody that is susceptible of being produced by said human subject when the latter is infected with, or has been infected with, said target infectious agent, the method comprising the following steps:

a) providing a kit or device for detecting said at least one target antibody directed against an infectious agent, which is capable of determining the humoral response due to the presence of said target infectious agent in said human subject and a volume V1 of the sample E1 of serum or plasma;

b) diluting the volume V1 with a volume D1 of diluent, with a dilution ratio R1 that is equal to V1/(V1+D1), the dilution ratio R1 being as 1.5R2≤R1≤5R2 with R2 being a dilution ratio used for a non-immunodepressed human subject, R2 being equal to V2/(V2+D2), with V2 and D2, respectively, being the volume of the sample E2 and the volume of diluent used for a non-immunosuppressed human subject, to obtain a diluted sample;

c) detecting said at least one target antibody in the resulting diluted sample and determining the possible presence of the humoral response.

2. The determination method according to claim 1, wherein:

the kit or device for detecting antibodies directed against said infectious agent, which is thus capable of determining the humoral response due to the presence of said target infectious agent in a human subject comprises:

a diluent in order to dilute the test samples of serum or plasma;

a dilution ratio R2 that is equal to V2/(V2+D2), adapted to a population of non-immunodepressed human subjects;

a dilution ratio R1 that is equal to V1/(V1+D1), adapted to a population of immunodepressed human subjects, with 1.5R2≤R1≤R2;

the method comprising a step of selecting the dilution ratio R1, taking into account the immunodepressed condition of the human subject from whom the sample of serum or plasma to be analyzed has been obtained.

3. A determination method for determining a humoral response due to the presence of a target infectious agent in an immunodepressed or non-immunodepressed human subject, by detecting, in a sample of serum or plasma of said human subject, at least one target antibody that is susceptible of being produced by said human subject when the latter is infected, or has been infected, with said target infectious agent, the method comprising the following steps:

providing a kit or device for detecting said at least one target antibody directed against an infectious agent, which is thus capable of determining the humoral response due to the presence of said target infectious agent in a human subject;

providing a volume V1 or V2 of test sample E1 or E2 of serum or plasma;

providing a diluent in order to dilute the volume V1 or V2 of test sample E1 or E2 of serum or plasma;

providing a dilution ratio R2 that is equal to V2/(V2+D2), adapted to a population of non-immunodepressed human subjects, with V2 and D2, respectively, being the volume of the sample E2 of serum or plasma and the volume of diluent used for a non-immunosuppressed human subject;

providing a dilution ratio R1 that is equal to V1/(V1+D1), with V1 and D2, respectively, being the volume of the sample E1 of serum or plasma and the volume of diluent used for an immunosuppressed human subject, R1 being adapted to a population of immunodepressed human subjects, with 1.5R2≤R1 5≤R2;

selecting the dilution ratio used as a function of the immunodepressed or not immunodepressed condition of the human subject from whom the sample of serum or plasma to be analyzed has been obtained: R1 is used if the human subject is immunodepressed, and R2 is used if the human subject is not immunodepressed;

diluting the volume V1 or V2 of test sample E1 or E2 of serum or plasma, with the selected dilution ratio and obtaining a diluted sample; and detecting said at least one target antibody in the resulting diluted sample, and determining the possible presence of the humoral response.

4. The determination method according to claim 1 or 3, wherein the increase in the dilution ratio R1 with respect to the dilution ratio R2 is obtained by increasing the volume V1 of the sample E1 of serum or plasma compared with the volume V2 of the sample E2 of serum or plasma used for a non-immunodepressed human subject.

5. The determination method according to claim 1 or 3, wherein the increase in the dilution ratio R1 with respect to the dilution ratio R2 is obtained by increasing the volume D1 of diluent compared with the volume D2 of diluent used for a non-immunodepressed human subject.

6. The determination method according to claim 1 or 3, wherein in step c), a signal is obtained and the conclusion as to the possible presence of the humoral response is positive if the signal obtained is higher than a reference signal S1, said reference signal S1 being greater than or equal to a reference signal S2 used for a sample of serum or plasma obtained from a non-immunodepressed human subject.

7. The determination method according to claim 1 or 3, wherein the detection of said at least one antibody is carried out in step c) under the same conditions as for detection carried out starting from a sample E2 of serum or plasma from a non-immunodepressed human subject.

8. The determination method according to claim 1 or 3, wherein in that the detection of said at least one target antibody is carried out in step c) by immunoassay.

9. The determination method according to claim 1 or 3, wherein the period between the start of the dilution of step b) and reaching the conclusion of step c) is 2 hours or less.

10. The determination method according to claim 1 or 3, wherein the infectious agent is a bacterium, a virus, a fungus, or a parasite.

11. A method for detecting, in a sample E1 of serum or plasma of a human subject, at least one target antibody that is susceptible of being produced by said human subject when the latter is infected with, or has been infected with, a target infectious agent, the method comprising the following steps:
 a) providing a kit or device for detecting said at least one target antibody directed against said target infectious agent and a volume V1 of the sample E1 of serum or plasma, b) diluting the volume V1 with a volume D1 of diluent, with a dilution ratio R1 that is equal to V1/(V1+D1), the dilution ratio R1 being as 1.5R2≤R1 5≤R2, with R2 being a dilution ratio used for a non-immunodepressed human subject, R2 being equal to V2/(V2+D2), with V2 and D2, respectively, being the volume of the sample E2 and the volume of diluent used for a non-immunosuppressed human subject, leading to a diluted sample;
 c) detecting said at least one target antibody in the resulting diluted sample.

12. A method for detecting, in a sample of serum or plasma of a human subject, at least one target antibody that is susceptible of being produced by said human subject when the latter is infected, or has been infected, with a target infectious agent, the method comprising the following steps:
 providing a kit or device for detecting said at least one target antibody directed against said target infectious agent in a human subject;
 providing a volume V1 or V2 of test sample E1 or E2 of serum or plasma;
 providing a diluent in order to dilute the volume V1 or V2 of test sample E1 or E2 of serum or plasma;
 providing a dilution ratio R2 that is equal to V2/(V2+D2), adapted to a population of non-immunodepressed human subjects, with V2 and D2, respectively, being the volume of the sample E2 of serum or plasma and the volume of diluent used for a non-immunosuppressed human subject;
 providing a dilution ratio R1 that is equal to V1/(V1+D1), with V1 and D2, respectively, being the volume of the sample E1 of serum or plasma and the volume of diluent used for an immunosuppressed human subject, R1 being adapted to a population of immunodepressed human subjects, with 1.5R2≤R1 5≤R2;
 selecting the dilution ratio used as a function of the immunodepressed condition, or otherwise of the human subject from whom the sample of serum or plasma to be analyzed has been obtained: R1 is used if the human subject is immunodepressed, and R2 is used if the human subject is not immunodepressed;
 diluting the volume V1 or V2 of test sample E1 or E2 of serum or plasma, with the selected dilution ratio and obtaining a diluted sample; and
 detecting said at least one target antibody in the resulting diluted sample.

* * * * *

SEQUENCE LISTING

<160> NUMBER OF SEQ ID NOS: 1

<210> SEQ ID NO 1
<211> LENGTH: 508
<212> TYPE: PRT
<213> ORGANISM: Artificial Sequence
<220> FEATURE:
<223> OTHER INFORMATION: Synthetic

<400> SEQUENCE: 1

Ser Val Leu Arg Tyr Asp Asp Phe His Thr Asp Glu Asp Lys Leu Asp
1               5                   10                  15

Thr Asn Ser Val Tyr Glu Pro Tyr Tyr His Ser Asp His Ala Glu Ser

```
             20                  25                  30
Ser Trp Val Asn Arg Gly Glu Ser Arg Lys Ala Tyr Asp His Asn
             35                  40                  45
Ser Pro Tyr Ile Trp Pro Arg Asn Asp Tyr Asp Gly Phe Leu Glu Asn
 50                  55                  60
Ala His Glu His His Gly Val Tyr Asn Gln Gly Arg Gly Ile Asp Ser
 65                  70                  75                  80
Gly Glu Arg Leu Met Gln Pro Thr Gln Met Ser Ala Gln Glu Asp Leu
                 85                  90                  95
Gly Asp Asp Thr Gly Ile His Val Ile Pro Thr Leu Asn Gly Asp Asp
                100                 105                 110
Arg His Lys Ile Val Asn Val Asp Gln Arg Gln Tyr Gly Asp Val Phe
                115                 120                 125
Lys Gly Asp Leu Asn Pro Lys Pro Gln Gly Gln Arg Leu Ile Glu Val
                130                 135                 140
Ser Val Glu Glu Asn His Pro Phe Thr Leu Arg Ala Pro Ile Gln Arg
145                 150                 155                 160
Ile Tyr Gly Val Arg Tyr Thr Glu Thr Trp Ser Phe Leu Pro Ser Leu
                165                 170                 175
Thr Cys Thr Gly Asp Ala Ala Pro Ala Ile Gln His Ile Cys Leu Lys
                180                 185                 190
His Thr Thr Cys Phe Gln Asp Val Val Val Asp Val Asp Cys Ala Glu
                195                 200                 205
Asn Thr Lys Glu Asp Gln Leu Ala Glu Ile Ser Tyr Arg Phe Gln Gly
                210                 215                 220
Lys Lys Glu Ala Asp Gln Pro Trp Ile Val Val Asn Thr Ser Thr Leu
225                 230                 235                 240
Phe Asp Glu Leu Glu Leu Asp Pro Pro Glu Ile Glu Pro Gly Val Leu
                245                 250                 255
Lys Val Leu Arg Thr Glu Lys Gln Tyr Leu Gly Val Tyr Ile Trp Asn
                260                 265                 270
Met Arg Gly Ser Asp Gly Thr Ser Thr Tyr Ala Thr Phe Leu Val Thr
                275                 280                 285
Trp Lys Gly Asp Glu Lys Thr Arg Asn Pro Thr Pro Ala Val Thr Pro
                290                 295                 300
Gln Pro Arg Gly Ala Glu Phe His Met Trp Asn Tyr His Ser His Val
305                 310                 315                 320
Phe Ser Val Gly Asp Thr Phe Ser Leu Ala Met His Leu Gln Tyr Lys
                325                 330                 335
Ile His Glu Ala Pro Phe Asp Leu Leu Leu Glu Trp Leu Tyr Val Pro
                340                 345                 350
Ile Asp Pro Thr Cys Gln Pro Met Arg Leu Tyr Ser Thr Cys Leu Tyr
                355                 360                 365
His Pro Asn Ala Pro Gln Cys Leu Ser His Met Asn Ser Gly Cys Thr
                370                 375                 380
Phe Thr Ser Pro His Leu Ala Gln Arg Val Ala Ser Thr Val Tyr Gln
385                 390                 395                 400
Asn Cys Glu His Ala Asp Asn Tyr Thr Ala Tyr Cys Leu Gly Ile Ser
                405                 410                 415
His Met Glu Pro Ser Phe Gly Leu Ile Leu His Asp Gly Gly Thr Thr
                420                 425                 430
Leu Lys Phe Val Asp Thr Pro Glu Ser Leu Ser Gly Leu Tyr Val Phe
                435                 440                 445
```

```
Val Val Tyr Phe Asn Gly His Val Glu Ala Val Ala Tyr Thr Val Val
    450                 455             460

Ser Thr Val Asp His Phe Val Asn Ala Ile Glu Glu Arg Gly Phe Pro
465             470                 475                 480

Pro Thr Ala Gly Gln Pro Pro Ala Thr Thr Lys Pro Lys Glu Ile Thr
            485                 490                 495

Pro Val Asn Pro Gly Thr Ser Pro Leu Leu Arg Tyr
            500             505
```